United States Patent [19]
Walker

[11] Patent Number: 5,273,054
[45] Date of Patent: Dec. 28, 1993

[54] PERMANENT DIAPHRAGM

[76] Inventor: John W. Walker, 29 Poplar St., Perkinston, Miss. 39573

[21] Appl. No.: 763,430

[22] Filed: Sep. 19, 1991

[51] Int. Cl.$^5$ ............................................. A61F 89/01
[52] U.S. Cl. .................... 128/837; 128/838; 128/839; 128/830
[58] Field of Search ............... 128/830, 831, 832, 833, 128/834, 835, 836, 837, 838, 839

[56] References Cited

U.S. PATENT DOCUMENTS

| | | | |
|---|---|---|---|
| 897,050 | 8/1908 | Beck | 128/834 |
| 3,774,600 | 11/1973 | Coonat | 128/831 X |
| 3,840,005 | 10/1974 | Walker | 128/839 |
| 4,237,893 | 12/1980 | Michaels | 128/839 X |
| 4,304,226 | 12/1981 | Drobish et al. | 128/832 |
| 4,860,746 | 8/1989 | Yoon | 128/830 |

FOREIGN PATENT DOCUMENTS 1163886  3/1984  Canada ............................ 128/832

*Primary Examiner*—Robert A. Hafer
*Assistant Examiner*—Sam Rimell

[57] ABSTRACT

This invention titled "Permanent Diaphragm" is a method of contraception. It is different from conventional diaphragms in that it is secured by suture to the cervix (mouth of the uterus). It is made of durable material that can be worn indefinitely. It can be inserted and can be removed as an office procedure.

1 Claim, 1 Drawing Sheet

PERMANENT DIAPHRAGM

DESCRIPTION OF THE INVENTION

Figure 1:
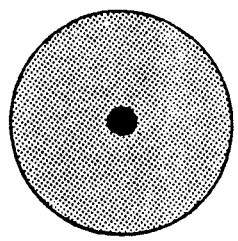
FIG. 1 depicts the permanent diaphragm, the principal and most pertinent component of the invention.

The material used for the permanent diaphragm, FIG. 1, is silicone sheeting. The material is approximately 3 cm in diameter and has a thickness of 0.2 mm. It has the characteristic of tissue paper. It is a durable material and has been used for several decades to repair defects in the body, for example, a hole in the bladder. It is left in the body permanently. The silicone sheeting does not pose risks as perhaps the silicone jel breast implants pose. The safety of the latter has been questioned recently. The integrity, durability, and safety of the reinforced silicone sheeting are not in question.

Figure 2:
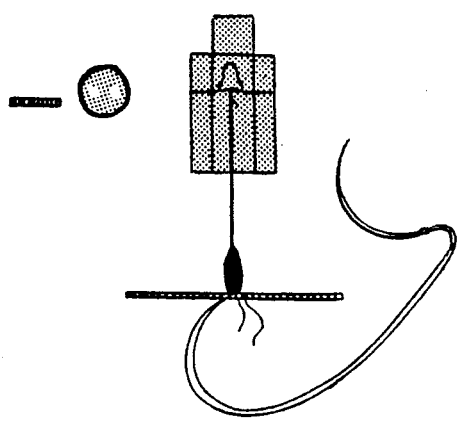
FIG. 2 depicts the permanent diaphragm with suture and needle attached to the lower end of the body of the stabilizing component. Also depicted is a side view and a frontal view of the securing button.
Figure 3:
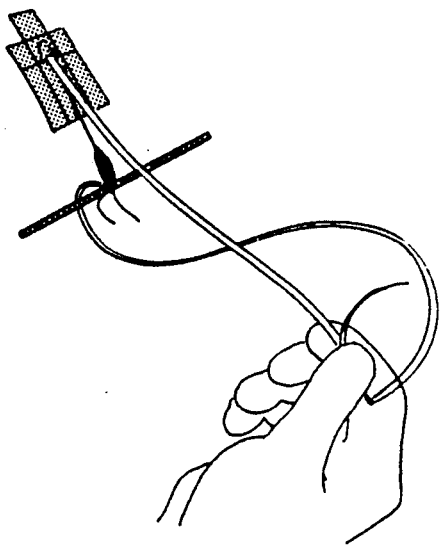
FIG. 3 depicts the insertion technique using a metal sound.
Figure 4:
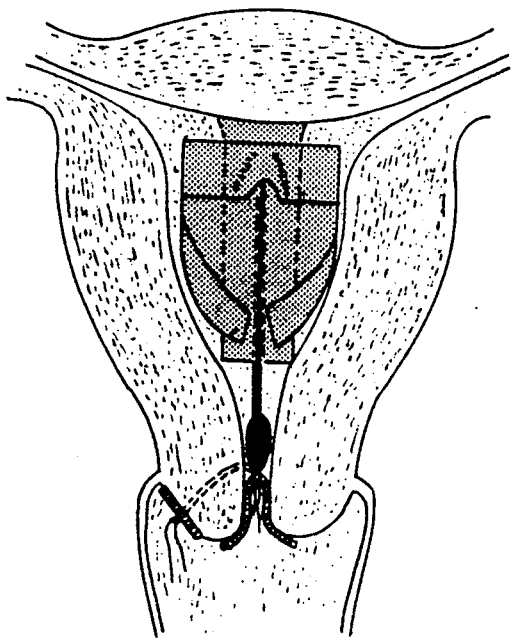
FIG. 4 depicts the permanent diaphragm secured in place. The different areas of the female reproductive tract are delineated, namely, the uterus, the cervix and the vagina.

FIG. 2 depicts the permanent diaphragm 1 attached to the stabilizing body 2. This latter component is likewise made of the same material as the permanent diaphragm. It also facilitates the placement of the diaphragm as depicted in FIGS. 3 and 4. The suture carried by a surgical needle is nylon 4. Nylon among other sutures has been permanently placed in the body for many years.

FIG. 3 depicts the insertion technique in which the silicone body 2 is mounted on a sound 5. The suture and needle 4 are held by the operator.

FIG. 4 depicts the permanent diaphragm 1 in place. The stabilizing silicone body 2 has been guided into place in the uterus 6. The needle with the nylon suture 4 has been passed through the lip of the cervix 7. The silicone button 3 has been threaded on the nylon suture 4 and tied firmly. The button 3 is constructed of reinforced silicone.

The excess nylon suture 4 has been cut and discarded. It can be noted that being in place the permanent diaphragm 1 acts locally at the level of the cervix 7.

What is claimed:

1. A method for permanent placement of a contraceptive device, comprising:

providing a contraceptive device including an apertured silicone mounting body, a circular silicone diaphragm attached to said body and a sutured needle attached to said diaphragm;

inserting a sound into the aperture of the mounting body;

inserting the sound, with said device, into a female uterus;

removing the sound; and inserting the sutured needle through the wall of said uterus and attaching a button to the exterior wall of said uterus with said sutured needle, so as to retain the mounting body and the diaphragm in the uterus.

* * * * *